United States Patent [19]

Sehring et al.

[11] Patent Number: 4,639,438
[45] Date of Patent: Jan. 27, 1987

[54] O,S-DIALKYL-O-(SUBSTITUTED PHENYL)-THIOLPHOSPHATES AS PESTICIDES

[75] Inventors: Richard Sehring; Wolfgang Buck, both of Ingelheim; Ricarda Prokic-Immel, Mainz; Sigmund Lust, Darmstadt, all of Fed. Rep. of Germany

[73] Assignee: Celamerck GmbH & Co. KG, Ingelheim am Rhein, Fed. Rep. of Germany

[21] Appl. No.: 839,036

[22] Filed: Mar. 12, 1986

Related U.S. Application Data

[63] Continuation of Ser. No. 678,224, Dec. 5, 1984, abandoned, which is a continuation of Ser. No. 503,675, Jun. 13, 1983, abandoned.

[30] Foreign Application Priority Data

Jun. 26, 1982 [DE] Fed. Rep. of Germany ....... 3223949

[51] Int. Cl.$^4$ ......................... A01N 57/14; C07F 9/18
[52] U.S. Cl. ..................................... 514/129; 558/194
[58] Field of Search ........................ 558/194; 514/129

[56] References Cited

FOREIGN PATENT DOCUMENTS 3223949 12/1983 Fed. Rep. of Germany ...... 558/194

Primary Examiner—Anton H. Sutto
Attorney, Agent, or Firm—Hammond & Littell, Weissenberger & Dippert

[57] ABSTRACT

Compounds of the formula

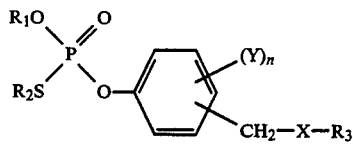

wherein
$R_1$ and $R_2$ which may be identical to or different from each other, are each straight or branched alkyl of 1 to 3 carbon atoms;
$R_3$ is alkyl of 1 to 8 carbon atoms;
X is sulfur or oxygen;
Y is chlorine, bromine or fluorine; and
n is 1 or 2.

The compounds are useful as pesticides.

6 Claims, No Drawings

O,S-DIALKYL-O-(SUBSTITUTED PHENYL)-THIOLPHOSPHATES AS PESTICIDES

This is a continuation of Ser. No. 678,224, filed Dec. 5, 1984, now abandoned; which in turn is a continuation of application Ser. No. 503,675, filed June 13, 1983, now abandoned.

This invention relates to novel esters of thiolphosphoric acid, to a method of preparing these compounds, to pesticidal compositions containing them as active ingredients, and to methods of using them as pesticides.

More particularly, the present invention relates to a novel class of thiolphosphates represented by the formula

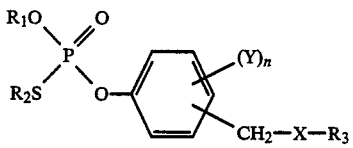

wherein
  $R_1$ and $R_2$ which may be identical to or different from each other, are each straight or branched alkyl of 1 to 3 carbon atoms;
  $R_3$ is alkyl of 1 to 8 carbon atoms;
  X is sulfur or oxygen;
  Y is chlorine, bromine or fluorine; and
  n is 1 or 2.
When n is 2, Y may be two identical or different halogens, as defined above.

A preferred subgenus is constituted by those compounds of the formula I wherein
  $R_1$ and $R_2$ are each independently straight or branched alkyl of 1 to 3 carbon atoms;
  $R_3$ is alkyl of 1 to 3 carbon atoms;
  X is sulfur or oxygen;
  Y is chlorine; and
  n is 1.

An especially preferred subgenus is constituted by those compounds of the formula I wherein $R_1$ is methyl or ethyl;
  $R_2$ is n-propyl or isopropyl;
  $R_3$ is methyl;
  X is sulfur or oxygen;
  Y is chlorine; and
  n is 1.

The compounds embraced by formula I may be prepared by a two-step process which comprises reacting a compound of the formula

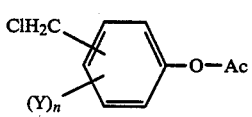

wherein
  Y and n have the meanings previously defined, and
  Ac is carboxylic acyl, at a temperature between 80° and 180° C., preferably between 100° and 140° C., in an autoclave with a compound of the formula $$R_3XH \quad \text{(III)}$$

wherein $R_3$ and X have the meanings previously defined, in the presence of a finely divided calcium carbonate or, when X is sulfur, in the presence of sodium carbonate or potassium carbonate, in an inert solvent, and optionally in the presence of an iodide such as sodium iodide, and reacting the resulting phenol intermediate of the formula

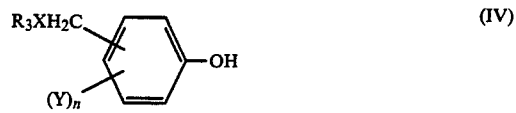

wherein $R_3$, X, Y and n have the meanings previously defined, either in the form of a phenolate or in the presence of an acid-binding agent, at a temperature between room temperature and the boiling point of the reaction mixture, preferably between 20° and 100° C., and in an inert solvent, with a phosphonic acid chloride of the formula

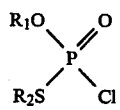

wherein $R_1$ and $R_2$ have the meanings previously defined.

When the first reaction step of the process is performed with a mercaptan or a mercaptide, that is, when X in formula III is sulfur, examples of suitable inert solvents are lower alkanols such as methanol. On the other hand, when the first reaction step is performed with an alcohol, that is, when X in formula III is oxygen, the alcohol of the formula III may itself serve as the solvent medium if provided in sufficient excess.

The reaction of the phenol of the formula IV with the phosphoric acid chloride of the formula V is carried out in conventional manner. The solvent medium may be, for example, toluene, dioxane, tetrahydrofuran, acetonitrile, methyl ethyl ketone or optionally water, or mixtures of these solvents. If a phenolate is used, it may be derived, for example, from an alkali metal base or from an organic base such as triethylamine, trimethylamine or ethylpiperidine. The phenolate need not be isolated; indeed, the phenolate may be prepared in situ by adding a solution of the amine to the mixture of IV, V and the solvent already prepared.

The compounds of formula I are oily substances. If desired, the crude product may be purified by conventional methods, such as by distillation under reduced pressure.

The starting compounds of the formula II may be obtained by reacting a corresponding compound of the formula

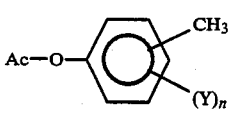

wherein Ac, Y and n have the meanings previously defined, in an excess of at least 50% with sulfuryl chloride in the presence of a radical-forming catalyst such as α,α'-azoisobutyric acid dinitrile, benzoyl peroxide, and in a solvent such as methylene chloride or carbon tetrachloride, at the boiling point of the reaction mixture.

The following examples illustrate the present invention and will enable others skilled in the art to understand it more completely. It should be understood, however, that the invention is not limited solely to the particular examples given below.

EXAMPLE 1
O-Ethyl-S-n-propyl-0-(4-chloro-2-methoxymethylphenyl)thiolphosphate

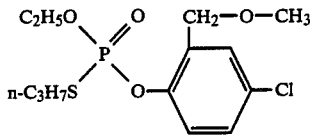

(a) 4-Chloro-2-methoxymethylphenol 219 g of 3-chloro-6-0-acetylbenzyl chloride were heated at 130° C. in an autoclave for 15 hours with 200 g of prepared chalk and 4 g of sodium iodide in 1000 ml of methanol. The pressure was not more than 15 bar. The reaction mixture was filtered, and the methanol was removed in a rotary evaporator. The residue was taken up in 300 ml of toluene, and the solution was washed with 100 ml of water. The organic phase was then stirred for 24 hours with 100 ml of 40% sodium hydrogen sulfite solution. The toluene phase was separated, the toluene was distilled off, and the residue was distilled under reduced pressure. Yield: 86.4% of theory, $Bp_{0.1\ mbar}$ 85°–87° C.

(b) End product 104 g (0.6 mol) of 4-chloro-2-methoxymethylphenol and 125 g of 0-ethyl-S-n-propylthiolphosphoric acid chloride are placed in 500 ml of toluene. At about 40° C., a solution of 63 g of triethylamine in 63 ml of toluene was added dropwise thereto. The resulting mixture was then allowed to react for 3 hours more at 60° C. and then stirred with 200 ml of ice water. The toluene phase was separated and concentrated by evaporation using a rotary evaporator. $Bp_{0.1\ mbar}$ 183° C.

According to thin-layer chromatography (1:1 acetone and heptane, developed with palladium chloride solution) the reaction product was virtually pure. Refraction index: $n_D^{25} = 1.5216$.

EXAMPLE 2
O-Ethyl-S-n-propyl-0-(2-chloro-4-methylthiomethylphenyl)-thiolphosphate

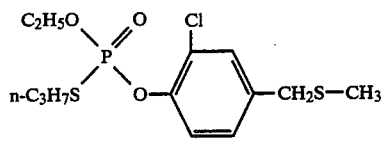

(a) 2-Chloro-4-methylthiomethylphenol 110 g (0.5 mol) of 2-chloro-4-chloromethylphenyl acetate were placed in 250 ml of methanol, and then a solution of 48 g of sodium methylmercaptide (0.65 mol) in 200 ml of methanol was added dropwise at about 5° to 10° C. The mixture was allowed to react for 3 hours at 50° C., then 30 g of potassium carbonate were added, and the resulting mixture was stirred for 2 hours more at 60° C. The reaction mixture was filtered and concentrated by evaporation in a rotary evaporator. The residue was taken up in 200 ml of toluene and extracted with 100 ml of 1N hydrochloric acid. The toluene phase was dried with sodium sulfate, and the toluene was distilled off using a rotary evaporator. Yield after distillation $Bp_{0.1\ mbar}$ 105°–108° C.) was 80 g (85% of theory).

(b) End product 32 g of triethylamine in 50 ml of toluene were added dropwise to 56.7 g of the phenol obtained in (a) and 62 g of 0-ethyl-S-n-propylthiophosphoric acid chloride in 250 ml of toluene, while the temperature was kept below 40° C. Then, the mixture was allowed to react for 4 hours at 60° C., and after cooling it was extracted with 100 ml of acidified ice water. The organic phase was dried with sodium sulfate and concentrated by evaporation in a rotary evaporator. The yield was virtually quantitative. According to thin-layer chromatography (eluant: acetone/heptane =1:1, developed with palladium chloride) the product was uniform. Refraction index: $n_D^{25} = 1.5495$.

The compounds of the formula I shown in the following table were prepared in analogy to the procedure described in Examples 1 and 2, respectively.

TABLE I

| Example | n | Y | $R_1$ | $R_2$ | $CH_2-X-R_3$ |
| --- | --- | --- | --- | --- | --- |
| 3 | 1 | 4-Cl | $CH_3$ | $CH_3$ | $2\text{-}CH_2\text{-}O\text{-}CH_3$ |
| 4 | 1 | 4-Cl | $CH_3$ | $CH_3$ | $2\text{-}CH_2\text{-}S\text{-}CH_3$ |
| 5 | 1 | 2-Cl | $CH_3$ | $C_2H_5$ | $4\text{-}CH_2\text{-}O\text{-}C_2H_5$ |
| 6 | 1 | 2-Cl | $C_2H_5$ | $C_2H_5$ | $4\text{-}CH_2\text{-}S\text{-}C_2H_5$ |
| 7 | 1 | 3-Cl | $C_2H_5$ | $n\text{-}C_3H_7$ | $4\text{-}CH_2\text{-}O\text{-}CH_3$ |
| 8 | 1 | 4-Cl | $C_2H_5$ | $n\text{-}C_3H_7$ | $3\text{-}CH_2\text{-}S\text{-}CH_3$ |
| 9 | 1 | 4-Cl | $C_2H_5$ | $n\text{-}C_3H_7$ | $2\text{-}CH_2\text{-}O\text{-}C_2H_5$* |
| 10 | 1 | 4-Cl | $C_2H_5$ | $n\text{-}C_3H_7$ | $2\text{-}CH_2\text{-}O\text{-}i\text{-}C_3H_7$** |
| 11 | 1 | 4-Cl | $CH_3$ | $n\text{-}C_3H_7$ | $2\text{-}CH_2\text{-}S\text{-}n\text{-}C_6H_{13}$ |
| 12 | 1 | 2-Cl | $n\text{-}C_3H_7$ | $n\text{-}C_3H_7$ | $4\text{-}CH_2\text{-}S\text{-}i\text{-}C_3H_7$ |
| 13 | 1 | 4-Cl | $C_2H_5$ | $n\text{-}C_3H_7$ | $3\text{-}CH_2\text{-}O\text{-}CH_3$ |
| 14 | 1 | 2-Cl | $C_2H_5$ | $n\text{-}C_3H_7$ | $5\text{-}CH_2O\text{-}CH_3$ |
| 15 | 1 | 2-Cl | $C_2H_5$ | $CH_3$ | $4\text{-}CH_2\text{-}S\text{-}CH_3$ |
| 16 | 1 | 4-Cl | $CH_3$ | $i\text{-}C_3H_7$ | $3\text{-}CH_2\text{-}O\text{-}C_2H_5$ |
| 17 | 1 | 4-Cl | $n\text{-}C_3H_7$ | $n\text{-}C_3H_7$ | $2\text{-}CH_2\text{-}O\text{-}CH_3$ |
| 18 | 1 | 4-Cl | $C_2H_5$ | $C_2H_5$ | $2\text{-}CH_2\text{-}O\text{-}CH_3$ |
| 19 | 1 | 2-Cl | $CH_3$ | $C_2H_5$ | $4\text{-}CH_2\text{-}O\text{-}i\text{-}C_3H_7$ |
| 20 | 1 | 4-F | $CH_3$ | $n\text{-}C_3H_7$ | $2\text{-}CH_2\text{-}O\text{-}CH_3$ |
| 21 | 1 | 4-Br | $C_2H_5$ | $n\text{-}C_3H_7$ | $3\text{-}CH_2\text{-}S\text{-}N\text{-}C_3H_7$ |
| 22 | 1 | 2-Br | $C_2H_5$ | $n\text{-}C_3H_7$ | $4\text{-}CH_2\text{-}O\text{-}n\text{-}C_3H_7$ |
| 23 | 1 | $2,5\text{-}Cl_2$ | $C_2H_5$ | $n\text{-}C_3H_7$ | $4\text{-}CH_2\text{-}O\text{-}CH_3$ |
| 24 | 1 | 2-Cl, 4-Br | $CH_3$ | $n\text{-}C_3H_7$ | $3\text{-}CH_2\text{-}S\text{-}CH_3$ |
| 25 | 1 | 4-Cl | $C_2H_5$ | $i\text{-}C_3H_7$ | $2\text{-}CH_2\text{-}O\text{-}C_8H_{17}$ |
| 26 | 1 | 2-F | $C_2H_5$ | $n\text{-}C_3H_7$ | $4\text{-}CH_2\text{-}S\text{-}i\text{-}C_4H_9$ |
| 27 | 1 | 2-Cl | $i\text{-}C_3H_7$ | $n\text{-}C_3H_7$ | $4\text{-}CH_2\text{-}S\text{-}t\text{-}C_4H_9$ |
| 28 | 1 | 4-Cl | $CH_3$ | $i\text{-}C_3H_7$ | $3\text{-}CH_2\text{-}O\text{-}n\text{-}C_5H_{11}$ |
| 29 | 1 | 3-Cl | $CH_3$ | $n\text{-}C_3H_7$ | $4\text{-}CH_2\text{-}S\text{-}i\text{-}C_3H_7$ |
| 30 | 1 | 3-Cl | $C_2H_5$ | $C_2H_5$ | $4\text{-}CH_2\text{-}O\text{-}C_2H_5$ |
| 31 | 1 | 5-Cl | $C_2H_5$ | $n\text{-}C_3H_7$ | $2\text{-}CH_2\text{-}S\text{-}CH_3$ |
| 32 | 1 | 6-Cl | $C_2H_5$ | $C_2H_5$ | $2\text{-}CH_3\text{-}S\text{-}CH_3$ |

*$n_D^{25} = 1.5149$
**$n_D^{25} = 1.5100$

The novel compounds are useful for controlling animal pests. They are contact and systemic pesticides, particularly against insects and mites, even some resistant strains.

Examples of pests which can be controlled by using the compounds of formula I include: *Musca domestica, Sitophilus granarius, Aphis fabae, tetranychus urticae, Prodenia litura, Tetranychus cinnabarinus* (including varieties resistant to phosphoric acid ester); and in the larval stage: *Aedes aegypti, Epilachna varivestis, Spodoptera littoralis, Plutella maculipennis.* In general, the compounds of the invention are characterized by a broad spectrum of activity.

A particular advantage is the low toxicity in mammals, which enables the novel compounds to be used to combat ectoparasites without any problem.

Biological activity

The effect against various pests was tested in the greenhouse in conventional manner.

TABLE II

| Compound | Mortality in % Pest/concentration of active ingredient in the spray liquor | | |
|---|---|---|---|
| | A/100 ppm | B/100 ppm | C/100 ppm |
| Example 1 | 100 | 100 | 100 |
| Example 2 | 100 | 100 | 99 |
| Example 3 | 100 | 100 | — |
| Example 5 | 100 | 100 | 98 |
| Example 9 | 100 | — | — |
| Example 10 | 100 | 100 | — |
| Example 14 | 100 | 100 | 100 |
| Example 16 | 98 | — | — |
| Example 19 | — | 100 | 96 |
| Example 21 | 100 | 100 | — |
| Example 23 | 100 | 100 | 100 |
| Example 27 | 100 | 100 | 100 |
| Example 28 | 99 | 100 | 100 |
| Example 30 | 100 | 100 | 100 |
| Example 32 | 100 | 100 | 100 |

Pests:
A: *Plutella Maculipennis*
B: *Prodenia litura*
C: *Tetranychus urticae*

Even at 20 ppm, the compounds according to the invention, used on a variety of pests, will still kill all the pests or at least a number which is sufficient for practical purposes.

For pesticidal purposes the compounds of the present invention are incorporated as active ingredients into conventional pesticidal compositions, that is, compositions consisting essentially of an inert carrier and an effective pesticidal amount of the active ingredient, such as emulsion concentrates, wettable powders, dusting powders or the like. The active ingredient content in these compositions is between 0.01 and 95% by weight, depending upon the manner in which they are to be applied. Thus, wettable powders, emulsion concentrates and other ultra low volume compositions, which are diluted with water prior to use to form sprayable suspensions or solutions containing 0.01 to 3% by weight of the active ingredient, have a high active ingredient content. On the other hand, dusting powders and the like, which are applied as such, have a relatively low active ingredient content in the range of 0.01 to 3% by weight.

The following examples illustrate a few pesticidal compositions comprising a compound of the present invention as an active ingredient and represent the best modes contemplated of using the invention.

EXAMPLE 33

Emulsion concentrate 20 parts by weight of O-ethyl-S-n-propyl-0-(4-chloro-2-methoxymethyl-phenyl)-thiolphosphate are dissolved in 75 parts by weight of xylene, and the solution is admixed with 5 parts by weight of nonylphenyl polyglycol ether. The resulting emulsion concentrate is diluted with water to form a sprayable aqueous emulsion containing 0.01 to 0.1% by weight of the active ingredient.

EXAMPLE 34

Dusting powder 2 parts by weight of O-ethyl-S-n-propyl-0-(2-chloro-4-methylthiomethyl-phenyl)-thiolphosphate are sprayed onto 98 parts by weight of kaolin, and the composition is ground into a homogeneous powder.

EXAMPLE 35

Wettable powder 25 parts by weight of O-ethyl-S-n-propyl-0-(4-chloro-2-methoxymethyl-phenyl)-thiolphosphate are sprayed onto 75 parts by weight of diatomaceous earth, 2 parts by weight of sodium naphthalene sulfonate are added, and the mixture is ground into a homogeneous powder. The powder is suspended in a sufficient amount of water to form a sprayable aqueous suspension containing 0.01 to 0.1% by weight of the active ingredient.

Any one of the other compounds embraced by formula I may be substituted for the particular active ingredient in Examples 33 through 35. Likewise, the amount of active ingredient in these illustrative examples may be varied to achieve the desired concentration, and the amounts and nature of the inert carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:
1. A compound of the formula

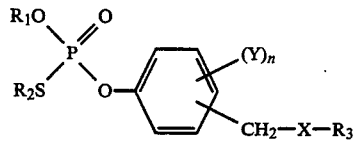

wherein
$R_1$ and $R_2$ are each independently straight or branched alkyl of 1 to 3 carbon atoms;
$R_3$ is alkyl of 1 to 8 carbon atoms;
X is oxygen;
Y is chlorine, bromine or fluorine; and
n is 1 or 2.
2. The method of killing pests, which comprises contacting said pests with an effective pesticidal amount of a compound of claim 1.
3. A compound of claim 1, where
$R_1$ and $R_2$ are each independently straight or branched alkyl of 1 to 3 carbon atoms;
$R_3$ is alkyl of 1 to 3 carbon atoms;
X is oxygen;
Y is chlorine; and
n is 1.
4. A compound of claim 1, where
$R_1$ is methyl or ethyl;
$R_2$ is n-propyl or isopropyl;
$R_3$ is methyl;
X is oxygen;
Y is chlorine; and
n is 1.
5. The compound of claim 1 which is O-ethyl-S-n-propy-0- (4-chloro-2-methoxymethylphenyl)-thiolphosphate.
6. A pesticidal composition consisting essentially of an inert carrier and an effective pesticidal amount of a compound of claim 1.

* * * * *